United States Patent [19]
Von Bebenburg et al.

[11] 3,956,344
[45] May 11, 1976

[54] PROCESS FOR THE PRODUCTION OF SUBSTITUTED 2-BENZOYLPYRIDINES

[75] Inventors: Walter Von Bebenburg, Buchschlag; Heribert Offermanns, Hanau, both of Germany

[73] Assignee: Deutsche Gold- und Silber-Scheideanstalt vormals Roessler, Germany

[22] Filed: Dec. 20, 1974

[21] Appl. No.: 534,866

[30] Foreign Application Priority Data
Dec. 24, 1973  Germany............................ 2364636

[52] U.S. Cl............................ 260/297 R; 424/263; 260/239.3 B; 260/294.9; 260/295 R
[51] Int. Cl.²........................................ C07D 213/50
[58] Field of Search ................................ 260/297 R

[56] References Cited
FOREIGN PATENTS OR APPLICATIONS
2,259,471   6/1973   Germany......................... 260/297 R

*Primary Examiner*—John D. Randolph
*Attorney, Agent, or Firm*—Cushman, Darby & Cushman

[57] ABSTRACT

2-benzoylpyridine and its derivatives substituted in the pyridine and/or benzene ring are prepared by oxidizing with hydrogen peroxide or other peroxide a compound of the formula:

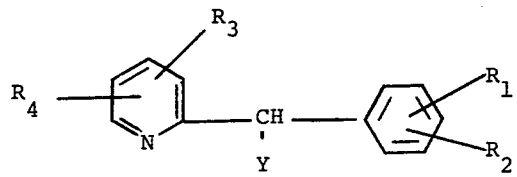

where $R_1$, $R_2$, $R_3$ and $R_4$ are hydrogen or a group inert under the oxidizing conditions and Y is cyano, carboxy or carbalkoxy in the presence of cyanate ion.

27 Claims, No Drawings

PROCESS FOR THE PRODUCTION OF SUBSTITUTED 2-BENZOYLPYRIDINES

It is known, for example to produce compounds of the Formula I:

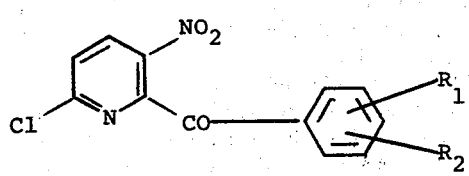

I wherein $R_1$ and $R_2$ are the same or different and are hydrogen, a halogen atom, e.g. of atomic weight 9 to 80, a trifluoromethyl group, nitro group, nitrite group, hydroxy group, lower alkyl group or lower alkoxy group by oxidation of a compound of the Formula II:

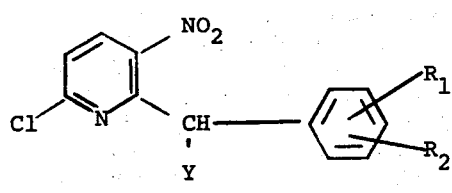

II by means of selenium dioxide or hydrogen peroxide. In Formula II Y means a nitrile group, a carboxy group or a lower carbalkoxy group and $R_1$ and $R_2$ have the above identified meanings, see von Bebenburg German Offenlegungsschrift No. 2,259,471 and von Bebenburg U.S. application Ser. No. 507,605 filed Sept. 19, 1974 as a Continuation-in-Part of von Bebenburg U.S. application Ser. No. 313,542 filed Dec. 8, 1972 and now abandoned. The entire disclosures of the two Bebenburg United States applications and the German Offenlegungsschrift are hereby incorporated by reference and relied upon. The compounds of the present invention are useful in preparing 6-azo-3H-1,4-benzodiazepines having spasmolytic and anxiolytic activity as shown in German Offenlegungsschrift No. 2,259,471.

The disadvantage of that process is that the oxidation with selenium dioxide produces a very impure product, which above all is not suited for further reaction because of the admixed selenoorganic compounds. The product can only be employed after repeated purifications. Besides the byproducts are extremely toxic and the process is uneconomical. On the contrary the known oxidation with hydrogen peroxide produces only a small part of the desired product. For the greater part the chlorine atom in the 6 position is hydrolyzed off under the alkaline conditions; to recover the desired products therefore the hydroxy compounds formed must subsequently be chlorinated in an additional reaction step. This process is also therefore uneconomical and protracted.

There has now been found a process for the production of benzoyl pyridine or substituted benzoyl pyridines by oxidizing a compound of Formula III:

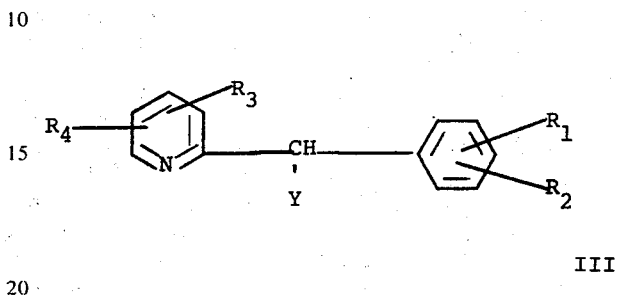

III where $R_1$, $R_2$, $R_3$ and $R_4$ are hydrogen or a group inert under the oxidizing conditions, e.g. halogen, nitro, trifluoromethyl, cyano, hydroxyl, alkyl (preferably lower alkyl, e.g. of 1 to 6 carbon atoms), alkoxy (preferably lower alkoxy e.g. of 1 to 6 carbon atoms) and Y is cyano, carboxy or lower carbalkoxy (preferably lower carbalkoxy of 1 to 6 carbon atoms in the alkoxy group) to form a compound of the Formula IV:

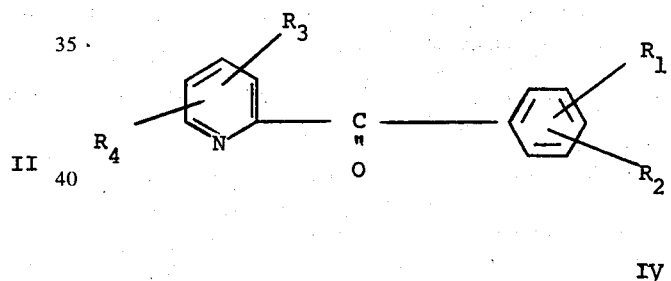

IV by utilizing hydrogen peroxide or other organic or inorganic peroxide which oxidation is carried out in the presence of cyanate ions.

The cyanate ions are added as cyanates. For example there can be used inorganic cyanates which are soluble in water or in mixtures of water and hydrophilic organic solvents. Especially there can be used alkali cyanates such as potassium cyanate or sodium cyanate. Also there can be used soluble alkaline earth metal cyanates, e.g. barium cyanate or there can be used ammonium cyanate.

The cyanate ion can be present in excess. For example it is favorable to use at least 1.5 moles of cyanate ion, for example 1.5 to 5 moles, per mole of compound of Formula III. Suitably the addition of the cyanate takes place as an aqueous solution. The concentration of the cyanate solution is not critical and can be for example between 5 and 60% preferably 10 to 40%. by weight. The addition of cyanate can take place before, simultaneously with, or after the addition of the oxidizing agent.

The time of addition of the cyanate with either simultaneous or subsequent addition of the oxidizing agent should be as short as possible and not exceed 70 minutes. A time between 30 and 50 minutes is convenient. With simultaneous addition of the oxidizing agent ($H_2O_2$, peroxide) the same time span is naturally valid. If the cyanate is already present in the reaction mixture and the oxidizing agent added subsequently then likewise the above mentioned time span is valid for the addition of the hydrogen peroxide or other peroxide.

The reaction is carried out for example in polar saturated organic solvents in which the presence of water is also necessary. As solvents there can be used for example aliphatic and cycloaliphatic ketones with 3 to 6 carbon atoms, e.g. acetone, methyl ethyl ketone methyl butyl ketone, methyl amyl ketone, diethyl ketone, methyl propyl ketone, cyclohexanone and cyclopentanore, aliphatic alcohols with 1 to 4 carbon atoms, e.g. methyl alcohol, ethyl alcohol, propyl alcohol, isopropyl alcohol, butyl alcohol, sec. butyl alcohol, t-butyl alcohol, amides, as well as alkyl and dialkyl amides of aliphatic carboxylic acids of 1 to 7 carbon atoms wherein the alkyl group or groups contain 1 to 4 carbon atoms, e.g. formamide, acetamide, methyl acetamide, dimethyl acetamide, butyl formamide, dimethyl formamide, ethyl acetamide, dipropyl formamide, propionamide, butyramide, caprylamide, the amides include tetramethyl urea, tetraethyl urea, dimethyl diethyl urea, esters of aliphatic carboxylic acids of 1 to 5 carbon atoms, e.g. alkanoic acids with aliphatic alcohols (e.g. alkanols) of 1 to 5 carbon atoms, e.g. methyl formate, ethyl formate, methyl acetate ethyl acetate, butyl acetate sec. butyl acetate, amyl acetate, methyl propionate, methyl butyrate, methyl valerate, ethyl valerate. Especially desirable is the use of ketones, for example acetone. The solvent of course should be liquid under the reaction conditions. The least amount of water based on 1 mole of the compound of Formula III is 250 ml.

At lower amounts of water, which means higher salt (cyanate) concentration two phases are formed.

The water can also be present in a large excess in relation to the organic solvent, for example two liters of water per mole of the compounds of Formula III. For example using one liter of acetone the total amount of solvent (acetone + total amount of water) can amount to 1.25 to 5 liters per mole of the compound of Formula III.

The process of the invention is preferably carried out at temperatures between 20° and 60°C., especially 35° to 45°C. but this can be varied to some extent.

Since the reaction is strongly exothermic, in a given case cooling must be provided for so that the above mentioned favorable temperature range is maintained.

As oxidizing agents there can be used hydrogen peroxide as well as inorganic and organic peroxides. The hydrogen peroxide is suitable added as a 5 to 35% solution, but this can be varied.

As peroxides there can be used known and conventional peroxide. For example there can be used neutral peroxides such as tert butyl peroxide, t-butyl hydroperoxide, cumene hydroperoxide, dicumyl peroxide, acid peroxides such as peracetic acid, perpropionic acid, perbutyric acid, perisobutyric acid, perbenzoic acid or alkali metal peroxides such as $Na_2O_2$. In case acid peroxides or potassium peroxide, or alkaline earth peroxides, e.g. barium peroxide or alkali peroxides are used it is necessary that the pH value be adjusted to the pH value of the diluted potassium cyanate (or other cyanate) solution. This pH is between 7 and 9.5.

The hydrogen peroxide or the peroxide is suitable added in excess based on the starting compound of Formula III. For example it is favorable to have a ratio of 1.5 to 3 moles of $H_2O_2$ per mole of the compound of Formula III.

The isolation of the reaction product takes place in customary manner. For example, the reaction product can be recovered in crystalline form by addition of water or aqueous ammonia. As a rule it is pure enough for further reactions.

The starting material of Formula III added according to the process of the invention can be unsubstituted or can be substituted in the benzene and/or the pyridine ring. There are used substituents which are inert under the reaction conditions, this means the substituents are not changed under the reaction condition. Such substituents for example include halogen atoms such as chlorine, bromine and fluorine (halogen of atomic weight 9 to 80), nitro groups, trifluoromethyl groups, cyano groups (nitrile groups), hydroxy groups, alkyl groups (for example lower alkyl groups having 1 to 6 carbon atoms, especially with 1 to 4 carbon atoms, e.g. methyl, ethyl, propyl, butyl, amyl, hexyl, isopropyl, sec. butyl, t-butyl), alkoxy groups (for example lower alkyl groups with 1 to 6 carbon atoms especially 1 to 4 carbon atoms, e.g. methoxy ethoxy, isopropoxy, propoxy, butoxy, amyloxy, hexoxy, isopropoxy, 2-ethylhexoxy. Both the pyridine ring and the benzene ring can contain one or two substituents just named. For example the pyridine ring can contain as substituents especially halogen atoms (e.g. chlorine, fluorine, bromine) and/or nitro groups, which are preferable in the 3-, 5- and 6 positions. Especially it is desirable for the pyridine ring to be substituted by a halogen atom (such as chlorine or fluorine) and a nitro group. The benzene ring can for example be substituted by one or two identical or different substituents wherein the preferable substituents are halogen atoms, especially chlorine, fluorine, or bromine, trifluoromethyl groups, nitrite, hydroxy, lower alkyl such as methyl or ethyl or lower alkoxy groups such as the methoxy or ethoxy group.

In case Y is a carbalkoxy group preferably the alkoxy portion has 1 to 6, most preferably 1 to 2 carbon atoms such as for example carmethoxy, carbethoxy, carbpropoxy, carbbutoxy, carbisobutoxy, carb sec. butoxy and carbhexoxy groups.

Examples of compounds which can be made according to the invention include 2-benzoyl-3-nitro-6-chloropyridine, 2-(o-chlorobenzoyl)-3-nitro-6-chloropyridine 2-(o-methylbenzoyl)-3-nitro-6-chloropyridine, 2-benzoylpyridine 2-benzoyl-3-nitro-6-hydroxypyridine, 2-(2',5'-dichlorobenzoyl)-3-nitro-6-chloropyridine, 2-(o-fluorophenyl)-3-nitro-6-chloropyridine, 2-benzoyl-3-nitro-6-bromopyridine, 2-benzoyl-3-nitro-6-fluoropyridine, 2-benzoyl-5-nitro-6-chloropyridine, 2-benzoyl-5-chloro-6-nitropyridine, 2-benzoyl-3-chloro-6-nitropyridine, 2-benzoyl-3-trifluoromethyl-6-chloropyridine, 2-benzoyl-3-cyano-6-chloropyridine, 2-benzoyl-3-methoxy-6-chloropyridine, 2-benzoyl-5-ethoxy-6-chloropyridine, 2-benzoyl-3, 6-dichloropyridine, 2-benzoyl-3, 6-difluoropyridine, 2-benzoyl-3, 6-dibromopyridine, 2-benzoyl-3-bromo-6-chloropyridine, 2-benzoyl-3-methyl-6-chloropyridine, 2-benzoyl-3, 5-dimethylpyridine, 2-benzoyl-3-ethyl-6-fluoropyridine, 2-benzoyl-3-butyl-6-chloropyridine, 2-benzoyl-3-hexyl-6-chloropyridine, 2-benzoyl-3-sec.- butyl-6-chloropyridine, 2-benzoyl-3-butoxy-6-chloropyridine, 2-benzoyl-3-hexoxy-6-chloropyridine, 2-(p-chlorobenzoyl)-3-nitro-6-chloropyridine, 2-(m-chlorobenzoyl)-3-nitro-6-chloropyridine, 2-(p-methylbenzoyl)-3-nitro-6-chloropyridine, 2-(3′,4′-dimethylbenzoyl)-3, 6-dichloropyridine, 2-(o-ethylbenzoyl)-3-nitro-6-chloropyridine, 2-(o-butylbenzoyl)-3-nitro-6-bromopyridine, 2-(p-hexylbenzoyl)-3-nitro-6-chloropyridine, 2-(o-trifluoromethylbenzoyl)-3-nitro-6-chloropyridine, 2-(o-cyanobenzoyl)-3-nitro-6-chloropyridine, 2-(o-hydroxybenzoyl)-3-nitro-6-chloropyridine, 2-(2′,4′-dihydroxybenzoyl)-3-nitro-6-chloropyridine, 2-(o-methoxybenzoyl)-3-nitro-6-chloropyridine, 2-(o-ethoxybenzoyl)-3-nitro-6-chloropyridine, 2-(o-butoxybenzoyl)-3-nitro-6-fluoropyridine, 2-(o-hexoxybenzoyl)-3-nitro-6-chloropyridine, As starting compounds of Formula III there can be used for example 2-(cyanophenylmethyl)-3-nitro-6-chloropyridine, 2-[cyano-(o-chlorophenyl)-methyl]-3-nitro-6-chloropyridine, 2-[cyano-(o-methylphenyl)-methyl]-3-nitro-6-chloropyridine, 2-(cyanophenylmethyl) pyridine, 2-(cyanophenylmethyl)-3-nitro-6-hydroxypyridine, 2-[cyano-(2′,5′-dichlorophenyl)-methyl]-3-nitro-6-chloropyridine, 2-[cyano-(o-fluorophenyl)-methyl]-3-nitro-6-chloropyridine, 2-(cyanophenylmethyl)-3-nitro-6-bromopyridine, 2-(cyanophenylmethyl)-3-nitro-6-fluoropyridine, 2-(cyanophenylmethyl)-5-nitro-6-chloropyridine, 2-(cyanophenylmethyl)-5-chloro-6-nitropyridine, 2-(cyanophenylmethyl)-3-chloro-6-nitropyridine, 2-(cyanophenylmethyl)-3-trifluoromethyl-6-chloropyridine, 2-(cyanophenylmethyl)-3-cyano-6-chloropyridine, 2-(cyanophenylmethyl)-3-methoxy-6-chloropyridine, 2-(cyanophenylmethyl)-5-ethoxy-6-chloropyridine, 2-(cyanophenylmethyl)-3, 6-dichloropyridine, 2-(cyanophenylmethyl)-3, 6-difluoropyridine, 2-(cyanophenylmethyl)-3, 6-dibromopyridine, 2-(cyanophenylmethyl)-3-bromo-6-chloropyridine, 2-(cyanophenylmethyl)-3-methyl-6-chloropyridine, 2-(cyanophenylmethyl)-3, 5-dimethylpyridine, 2-(cyanophenylmethyl)-3-ethyl-6-fluoropyridine, 2-(cyanophenylmethyl)-3-butyl-6-chloropyridine, 2-(cyanophenylmethyl)-3-hexyl-6-chloropyridine, 2-(cyanophenylmethyl)-3-sec.butyl6-chloropyridine, 2-(cyanophenylmethyl)-3-butoxy-6-chloropyridine, 2-(cyanophenylmethyl)-3-hexoxy-6-chloropyridine, 2-[cyano-(p-chlorophenyl)-methyl]-3-nitro-6-chloropyridine, 2-[cyano-(m-chlorophenyl)-methyl]-3-nitro-6-chloropyridine, 2-[cyano-(p-methylphenyl)-methyl]-3-nitor-6-chloropyridine, 2-[cyano-(3′,4′-dimethylphenyl)-methyl]-3, 6-dichloropyridine, 2-[cyano-(o-ethylphenyl)-methyl]-3-nitro-6-chloropyridine, 2-[cyano-(o-butylphenyl)-methyl]-3-nitro-6-bromopyridine, 2-[cyano-(p-hexylphenyl)-methyl]-3-nitro-6-chloropyridine, 2-[cyano-(o-trifluoromethylphenyl)methyl]-3-nitro-6-chloropyridine, 2-[cyano-(o-cyanophenyl)methyl]-3-nitro-6-chloropyridine, 2-[cyano-(o-hydroxyphenyl)-methyl]-3-nitro-6-chloropyridine, 2-[cyano-(2′,4′-dihydroxyphenyl)-methyl]-3-nitro-6-chloropyridine, 2-[cyano-(o-methoxyphenyl)-methyl]-3-nitro-6-chloropyridine, 2-[cyano-(o-ethoxyphenyl)-methyl]-3-nitro-6-chloropyridine, 2-[cyano-(o-butoxyphenyl)-methyl]-3-nitro-6-fluoropyridine, 2-[cyano-(o-hexoxyphenyl)-methyl]-3-nitro-6-chloropyridine, 2-[carboxy-(o-chlorophenyl)-methyl]-3-nitro-6-chloropyridine, 2-(carboxyphenylmethyl)-3-nitro-6-chloropyridine, 2-[carboxy-(o-methylphenyl)-methyl]-3-nitro-6-chloropyridine, 2-(carboxyphenylmethyl) pyridine, 2-(carboxyphenylmethyl)-3-nitro-6-hydroxypyridine, 2-(carbmethoxyphenylmethyl)-3-nitro-6-chloropyridine, 2-[carbethoxy-(o-chlorophenyl)-methyl]-3-nitro-6-chloropyridine, 2-[carbbutoxy-(o-methylphenyl)-methyl]-3-nitro-6-chloropyridine, 2-[carbhexoxy-(o-fluorophenyl)-methyl]-3-nitro-6-chloropyridine.

The starting compounds of Formula III can be made by the process described in German Offenlegungsschrift No. 2,259,471 pages 20–21 (and in von Bebenburg U.S. Application Ser. No. 507,605, pages 23–25). For example a compound of the formula:

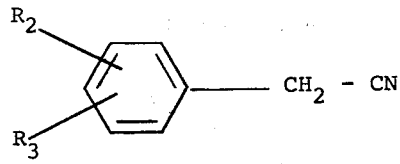

or:

$$R_2, R_3 \text{—phenyl—} CH_2 - CO_2R_6$$

where $R_6$ is hydrogen or a lower alkyl group is first reacted with an active alkali compound such as sodamide, potassium amide, sodium hydride or sodium in finely divided form in an inert solvent such as dioxane, dimethyl formamide, or benzene and then there is added dropwise the calculated amount of 2,6-dichloro-3-nitropyridine dissolved in the same solvent with stirring and a nitrogen atmosphere. In many cases it is suitable to change the order of addition, for example, to add the alkali compound to a solution of the phenylacetic or benzyl cyanide derivative and 2,6-dichloro-3-nitropyridine. The generally exothermic reaction leads to the alkali salts of the compounds of Formula III. Such salts are colored strongly blue to violet.

After the end of the reaction this is filtered with suction, washed, dissolved in water and treated with diluted glacial acetic acid until the disappearance of the intrinsic color. The compound of Formula III customarily crystallizes in sufficient purity.

The 2-[α-cyano)-o-chlorobenzyl]-3-nitro-6-chloropyridine is recovered, for example, as follows:

To a solution of 120 grams of o-chlorobenzyl cyanide in 1.5 liters of dioxane there were added at 45°C. with stirring in a nitrogen atmosphere 42 grams of sodium hydride (80% in white oil). Then the mixture was stirred for 45 minutes more at this temperature. The solution was then cooled and at 20° to 22°C. there were dropped in within 30 minutes 140 grams of 2,6-dichloro-3-nitropyridine in 500 ml of dioxane. Further reaction was permitted for three hours at this temperature. The deeply colored sodium salt was filtered off, washed with dioxane dissolved in water/methanol (1:1 by volume) and diluted acetic acid added until the color changed. The desired compound crystallized out, was filtered off with suction and thoroughly washed with methanol, M.P. 174° – 175°C., Yield 91 grams.

Unless otherwise indicated all parts and percentages are by weight.

EXAMPLE 1

2-benzoyl-3-nitro-6-chloropyridine

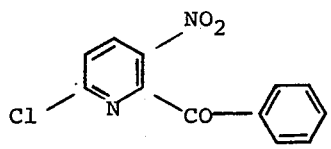

Five hundred forty eight grams (2 moles) of 2-(cyanophenylmethyl)-3-nitro-6-chloropyridine were suspended in 3 liters of acetone and these were simultaneously dropped in at 37°C. a solution of 325 grams of potassium cyanate (4 moles) in 1 liter of water and a solution of 435 ml of 30% $H_2O_2$ (4.05 moles) in 800 ml of water. The reaction vessel was cooled with ice water. Both solutions were added within 45 minutes. After the end of the addition the color of the solution turned from the initial permanganate color (violet) solution to a light yellow. The solution was cooled in an ice bath to 15°C., then 600 grams of ice, 300 ml of 25% aqueous ammonia and 1 liter added with stirring. Yellow crystals separated out. They were filtered off with suction after 1 hour and washed with water. After boiling with 4 parts of methanol per part of crystals, cooling and filtering with suction there was obtained the pure 2-benzoyl-3-nitro-6-chloropyridine, M.P. 107°C.

EXAMPLE 2

2-(o-chlorobenzoyl)-3-nitro-6-chloropyridine

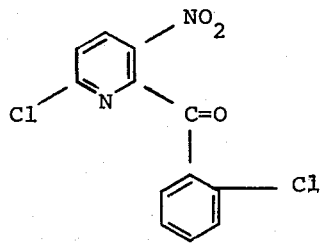

Six hundred sixteen grams (2 moles) of 2-[cyano-(o-chlorophenyl)-methyl]-3-nitro-6-chloropyridine were oxidized using the same procedure as in Example 1. The product was recrystallized from 15 parts of methanol (per part of product). Yield of 2-(o-chlorobenzoyl)-3-nitro-6-chloropyridine 70% M.P. 101°C.

EXAMPLE 3

2-(o-Methylbenzoyl)-3-nitro-6-chloropyridine

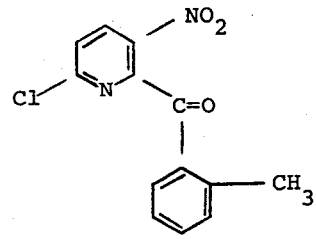

Ten grams of 2-[cyano-(o-methylphenyl)-methyl]-3-nitro-6-chloropyridine were oxidized using the same procedure as in Example 1. The reaction product was recrystallized from 5 parts of methanol (per part of 2-(o-methylbenzoyl)-3-nitro-6-chloropyridine reaction product). Yield 4 grams M.P. 111–112°C.

What is claimed is:

1. In a process for the production of a 2-benzoyl pyridine of the Formula:

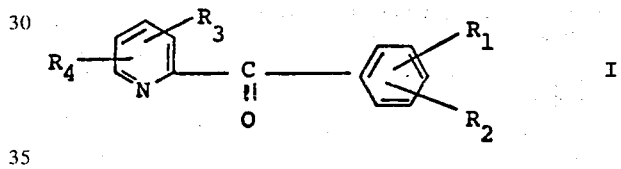

comprising oxidizing a compound of the Formula:

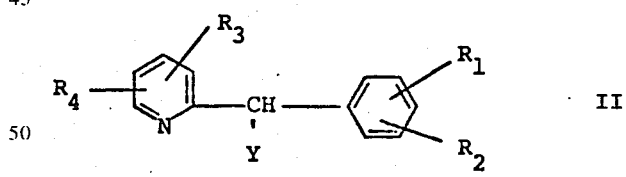

wherein each of $R_1$, $R_2$, $R_3$ and $R_4$ is hydrogen, halogen, nitro, trifluoromethyl, cyano, hydroxyl, alkyl or alkoxy and Y is cyano, carboxy or lower carbalkoxy, the improvement comprising carrying out the oxidation with a peroxide in a polar, saturated organic solvent in the presence of at least 250 ml of water per mole of compound of formula II in the presence of an alkali cyanate, alkaline earth metal cyanate or ammonium cyanate to provide cyanate ions with the proviso that when the cyanate is added simultaneously with or subsequent to the addition of the peroxide, the addition of the cyanate takes place within 70 minutes.

2. The process of claim 1 wherein the peroxide is hydrogen peroxide, alkali peroxide, alkyl peroxide, aryl peroxide or peralkanoic acid.

3. The process of claim 1 wherein the cyanate ions are supplied by alkali metal cyanate.

4. The process of claim 1 wherein $R_1$, $R_2$, $R_3$ and $R_4$ are hydrogen, halogen of atomic weight 9 to 80, nitro, trifluoromethyl, cyano, hydroxyl, alkyl of 1 to 6 carbon atoms or alkoxy of 1 to 6 carbon atoms.

5. The process of claim 4 where Y is cyano.

6. The process of claim 1 where the cyanate ions are provided by potassium cyanate.

7. The process of claim 6 wherein the peroxide is hydrogen peroxide.

8. The process of claim 1 wherein $R_3$ is a nitro group in the 3-position and $R_4$ is a halogen atom in the 6 position.

9. The process of claim 1 wherein $R_3$ and is hydrogen, halogen of atomic weight 9 to 80, nitro, trifluoromethyl, cyano, hydroxy, lower alkyl or lower alkoxy and $R_4$ is halogen of atomic weight of 9 to 80.

10. The process of claim 9 where $R_4$ is chlorine.

11. The process of claim 9 where $R_1$ and $R_2$ are hydrogen.

12. The process of claim 9 wherein one of $R_1$ and $R_2$ is hydrogen and the other is halogen or lower alkyl.

13. The process of claim 9 wherein the benzoyl pyridine prepared is 2-benzoyl-3-nitro-6-chloropyridine.

14. The process of claim 13 wherein the compound oxidized is 2-(cyanophenylmethyl)-3-nitro-6-chloropyridine.

15. The process of claim 9 wherein the benzoyl pyridine prepared is 2-(o-chlorobenzoyl)-3-nitro-6-chloropyridine and the compound oxidized is 2-[cyano-(o-chlorophenyl)-methyl]-3-nitro-6-chloropyridine.

16. The process of claim 9 wherein the benzoyl pyridine prepared is 2-(o-methylbenzoyl)-3-nitro-6-chloropyridine and the compound oxidized is 2-[cyano-(o-methylphenyl)-methyl]-3-nitro-6-chloropyridine.

17. The process of claim 1 carried out at 20° to 60°C.

18. The process of claim 17 wherein the peroxide is hydrogen peroxide.

19. The process according to claim 1 carried out at 35° to 45°C.

20. The process according to claim 1 wherein the temperature is 20° to 60°C. and the water is present in an amount of 250 ml to 2 moles per mole of compound of formula II.

21. The process of claim 1 wherein per liter of organic solvent the water is sufficient to provide up to a total of 5 liters of solvent per liter of organic solvent.

22. The process of claim 1 wherein at least one of $R_3$ and $R_4$ is chlorine.

23. The process of claim 1 wherein the temperature is 20° to 60°C. and there is used 1.5 to 5 moles of cyanate ion and 1.5 to 3 moles of peroxide per mole of compound of formula II.

24. The process of claim 23 wherein the cyanate is added prior to adding the peroxide.

25. The process of claim 23 wherein the cyanate is added simultaneously with adding the peroxide.

26. The process of claim 23 wherein the cyanate is added after adding the peroxide.

27. The process of claim 1 wherein $R_3$ is a nitro group in the 3-position, $R_4$ is a halogen atom in the 6-position, $R_1$ is a hydrogen, halogen or lower alkyl and $R_2$ is hydrogen.

* * * * *